United States Patent
Ohthuki et al.

Patent Number: 5,855,612
Date of Patent: Jan. 5, 1999

[54] BIOCOMPATIBLE TITANIUM IMPLANT

[75] Inventors: Chikara Ohthuki, Okayama; Akiyoshi Osaka, 416-1, Ohdara-cho, Okayama-shi, Okayama; Hirohisa Iida, Okayama; Keizo Ohta, Okayama, all of Japan

[73] Assignees: Ohta Inc.; Akiyoshi Osaka, both of Okayama, Japan

[21] Appl. No.: 644,747

[22] Filed: May 10, 1996

[30] Foreign Application Priority Data

May 12, 1995 [JP] Japan .................... 7-138481

[51] Int. Cl.⁶ .................... A61F 2/02
[52] U.S. Cl. .................... 623/11; 623/16
[58] Field of Search .................... 623/11, 16, 18, 623/20, 22

[56] References Cited

U.S. PATENT DOCUMENTS

| | | | |
|---|---|---|---|
| 5,045,318 | 9/1991 | Tengvall et al. | 424/422 |
| 5,152,993 | 10/1992 | Bjursten et al. | 424/422 |
| 5,612,049 | 3/1997 | Li et al. | 424/422 |

FOREIGN PATENT DOCUMENTS 1-275766  11/1989  Japan .

OTHER PUBLICATIONS

Author: Bengt Walivaara; Title: "An In–vitro Study of $H_2O_2$–treated Titanium Surfaces in Contact With Blood Plasma and a Simulated Body Fluid"; Date: 1993; Pertinent pp. 141–148.

Author: Chikara Ohtsuki; Title: "Mechanism of Apatite Formation on $CaO-SiO_2-P_2O_5$ Glasses in a Simulated Body Fluid"; Date: 1992; Pertinent pp. 84–92.

*Primary Examiner*—Debra S. Brittingham
*Assistant Examiner*—John M. Black
*Attorney, Agent, or Firm*—Koda and Androlia

[57] ABSTRACT

A biocompatible titanium implant with a modified exterior surface having a covering layer that comprises a hydrated titania gel. The exterior surface of the titanium implant is processed by a hydrogen peroxide aqueous solution that contains metal ions which not only promotes a reaction between the titanium implant and the hydrogen peroxide aqueous solution but also provides a high apatite formation ability to the hydrated titania gel on the surface of the implant.

5 Claims, 10 Drawing Sheets

BIOCOMPATIBLE TITANIUM IMPLANT

BACKGROUND OF THE INVENTION

1. Field of the Invention

The present invention relates to biocompatible titanium implant for use in dental and orthopedic surgery.

2. Prior Art

Titanium and titanium alloys are lightweight and have superior corrosive resistant properties when exposed to body tissues and body fluids. In addition, titanium and titanium alloys are ideal for use as artificial bones or implant materials (thus called "titanium implant material" in this specification) because they cause less inflammation, hypersensitivity, and allergic reaction when they come in contact with body tissues and body fluids. Titanium and titanium alloys are used for clinical materials for an artificial hip joint, knee joint, osteosynthesis and artificial tooth roots. However, titanium and titanium alloys lack the property to adhere to human bone or coalesce to bone tissue. Therefore, when the titanium and titanium alloy implants are implanted in the body for a long period of time, the metal implant can become detached itself and slip off of the bone.

On the other hand, inorganic materials such as bioactivated glass and hydroxyapatite are known to coalesce with bone tissue in the body. In particular, bioactivated glass is an ideal clinical material needed to bond materials to body tissues. Bioactivated glass has the property to form an apatite layer on its surface in the body or simulated body fluids that contain calcium and phosphoryl ion, and the apatite layer enables bioactivated glass to coalesce to body tissues. However, in many cases, bioactivated glass has lacked sufficient dynamic mechanical properties like toughness. Rather, the titanium and titanium alloys can fulfill these dynamic mechanical properties. Therefore, development of a material has been pursued that has not only the dynamic mechanical properties of metal materials but the bioactivity as of inorganic substance.

For this purpose, titanium implant materials that are spray-coated or sintered with a surface layer of calcium phosphoryl ceramics such as bioactive glass or hydroxyapatite have been proposed. However, the surface layer of the bioactivated material adheres poorly to the titanium implant, and complex production processes are needed to improve adhesion.

Japanese Patent Application Laid-Open No. 1-275766 discloses a solution of such problems and provides an improvement in adhesion of a metallic material to the bioactive layer. The production process in this prior art includes: a step of adding a super fine powder of hydroxyapatite to a hydrolysis solution of alkylsilicate to make a sol, a step of applying the thus obtained sol to the surface of the metal with a dry coating of a titanium alkoxyde solution, and a step of drying the coating of the sol and bake it at a proper temperature. Thus, this process is complicated.

A method for making the surface of a titanium or titanium alloys into a hygroscopic gel has been recognized. This method, however, uses a high concentration alkaline aqueous solution and a heat treatment conducted at a temperature as high as 600° C., making the process very complex. Furthermore, during the high temperature heating process, there exists the possibility that the mechanical properties of titanium and titanium alloy are damaged.

Another method for making the surface of titanium or titanium alloy into a hygroscopic gel is reported by B. Walivaara, I. Lundstrom and P. Tengvall in Clinical Materials (Vol. 12, pages 141–148). However, the thickness of the apatite layer, which is formed on the surface of a test sample after 72 hours of processing, is 12 nm, extremely thin; and a sufficient improvement of affinity to the body is not obtained.

SUMMARY OF THE INVENTION

Accordingly, the object of the present invention is to provide the surface of a metallic material with bioactivity so that the metallic material can bond with human tissue, particularly with bone tissue, using a simple and conventional low-temperature heating procedure without causing any damage in mechanical properties of metallic materials for artificial bones.

The inventors of this application have studied solutions for the problems in the prior art and have discovered that the addition of metal ions to a hydrogen proxside aqueous solution in which the titanium implant materials are soaked, provides biocompatibility (bioactivity). The invention of this application is a result of additional research and studies conducted based upon the findings above.

In a typical mode of the present invention, the biocompatible titanium implant has a chemically modified surface which is achieved by being immersed in a hydrogen peroxide aqueous solution that contains metal ions which promote a production of reaction layer on the surface of the implant and provides a high apatite formation ability to a hydrated titania gel on the surface of the implant.

The titanium implant according to the present invention has a layer that contains hydrated titania gel which is produced by the surface treatment methods conducted on the surface of the implant as described below:

Titanium implants in the present invention are defined as products of any shape made of titanium or titanium alloys to be used inside the (human) body. The surface of the titanium implant material becomes a hydrated titania gel; and the titanium implant materials can be used in any shape and application as long as they maintain their essential mechanical properties and keep harmless in the body. For example, they can be formed in a column, plate, block, sheet, fiber, or pellet shape; and stem for total hip joints, bone fibers, artificial vertebra, artificial intervertebral discs, plates and bone screws are available as the types of products.

The concentration of hydrogen peroxide in a hydrogen peroxide aqueous solution, which is used for processing the surface of titanium materials, is preferably 5 wt % or higher. In particular, if the processing is required to be completed in a short period of time, then the desirable concentration is higher than 30 wt %. The desirable temperature of the hydrogen peroxide aqueous solution, which has a concentration of 30 wt %, is between 30°–90° C. If the temperature exceeds 90° C., then the hydrogen peroxide suffers self-decomposition. On the other hand, if the temperature is lower than 30° C., the surface of the material cannot be processed sufficiently.

The substance to be added to hydrogen peroxide aqueous solution should be soluble. It should promote the reaction of the titanium material and hydrogen peroxide; in addition, it should apply high apatite forming capability to the hydrated titania gel which is formed on the surface of the titanium material. The most favorable results can be obtained from Ta, Sn and Ti compounds. Favorable results are also obtained by using chlorides and nitrates chlorides which include those of Si, Zr, Li and Na.

With the methods and material described above, it is possible to provide the surface of metal material, which has superior mechanical properties, with bioactivity at a temperature of 100° C. or less, thus using the metal material as implants which are suitable for artificial bone materials especially needed to bond with bones.

By adopting the method of the present invention, the titanium material forms apatite layers on its surface in the simulated body fluid which contains calcium ion and phosphate ions and it does in the body as well. Therefore, the obtained titanium implant in the present invention is able to unify with the body tissues through the apatite layer inside the body. In particular, it can unify not only with the hard tissue of the body such as bone and teeth but also with the soft tissue of the body such as skin and muscle.

BRIEF DESCRIPTION OF THE DRAWINGS

FIG. 4 shows the scanning electron micrographs of the titanium metal plates with the surface treated with a hydrogen peroxide aqueous solution that contains Ta ions, wherein

FIG. 5 shows the scanning electron micrographs of the titanium alloy plates with the surfaces thereof processed by a hydrogen peroxide aqueous solution that contains Sn ions, wherein

FIG. 6 shows the scanning electron micrographs of the titanium alloy plates with the surface thereof processed by a hydrogen peroxide aqueous solution that contains Ta ions, wherein

FIG. 7 shows the scanning electron micrographs of the titanium metal plate in which the surface is processed by a hydrogen peroxide aqueous solution which contains no metal ions therein, wherein

DETAILED DESCRIPTION OF THE PREFERRED EMBODIMENTS

The present invention will be described below via the embodiments thereof. The present invention should not be limited to the embodiments.

Figure 1:
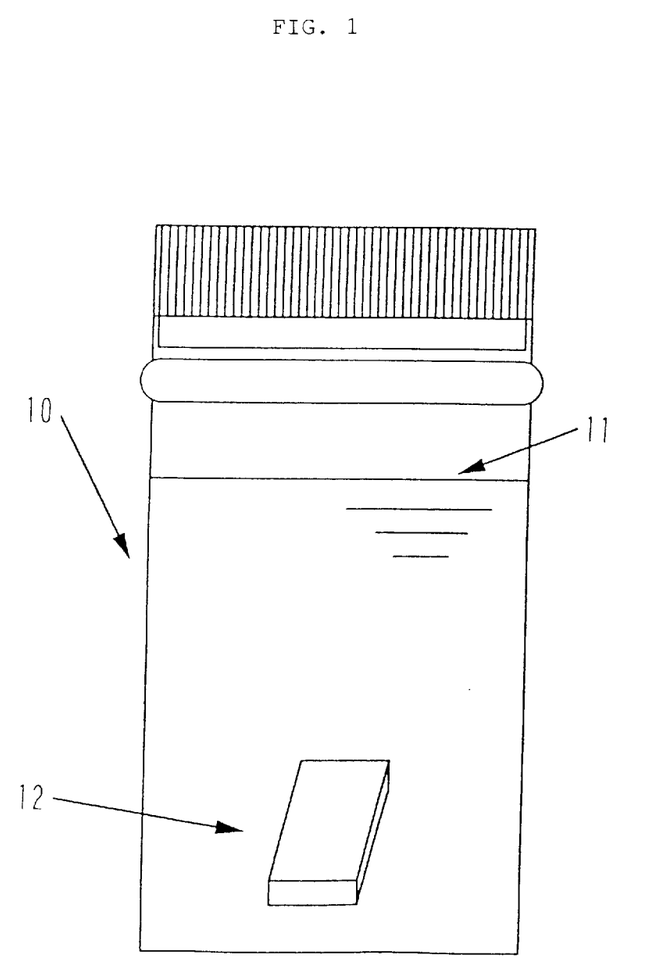
FIG. 1 illustrates the surface processing test using a titanium metal plate.

Embodiment using titanium metal plate processed by a hydrogen peroxide solution that contains Ta ions So as to be used as a reaction solution, TaCl5 is dissolved into a hydrogen peroxide aqueous solution containing 30 wt % of $H_2O_2$ so that the solution has a concentration of 5 mmol/dm$^3$. As shown in FIG. 1, the thus obtained solution 11 in the amount of 30 ml is put in a polystyrene bottle 10, and a titanium metal plate (15×10×1 mm) 12 is placed in the medium 11. The bottle is retained for 24 hours at 60° C. After 24 hours, the titanium metal plate 12 is removed from the solution 11, cleaned using distilled water, and dried at room temperature.

An aqueous solution is prepared by the method described in Journal of Non-Crystalline Solids, written by C. Otsuki, et al., Vol. 143, p.84–92, (1992). The obtained solution contains the metal ions as shown in Table 1 in the concentration as in Table 1. The solution is adjusted to have a pH of 7.25 by using Tris (hydroxymethyll) aminomethane aqueous solution and hydrochloric acid. This solution is used as the simulated body fluid.

Figure 2:
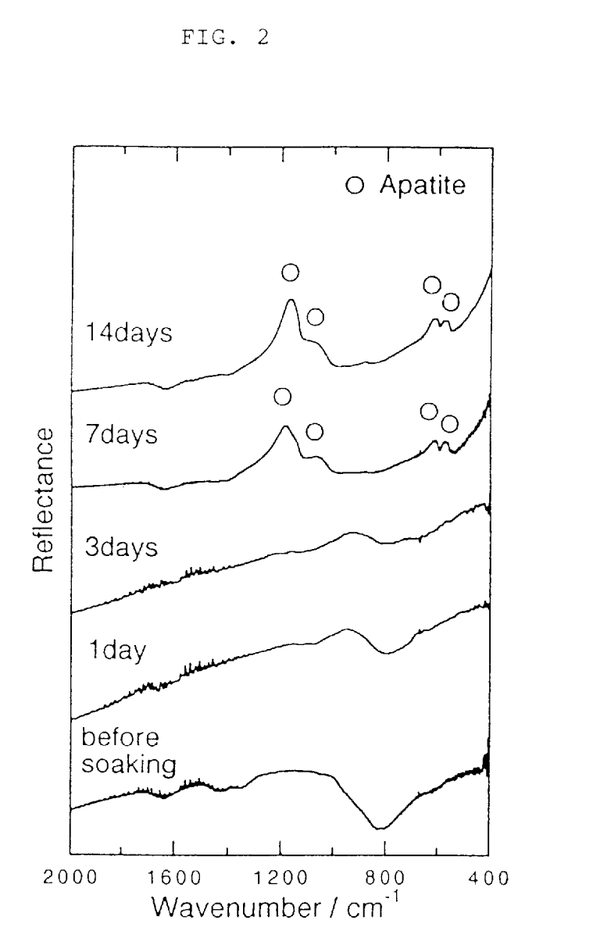
FIG. 2 shows the Fourier Transformation Infrared Rays Reflection Spectrum (FT-IR Reflection Spectrum) of the titanium metal plate whose surface is treated with a hydrogen peroxide aqueous solution containing Ta ions, after being immersed in the simulated body fluid.
Figure 3:
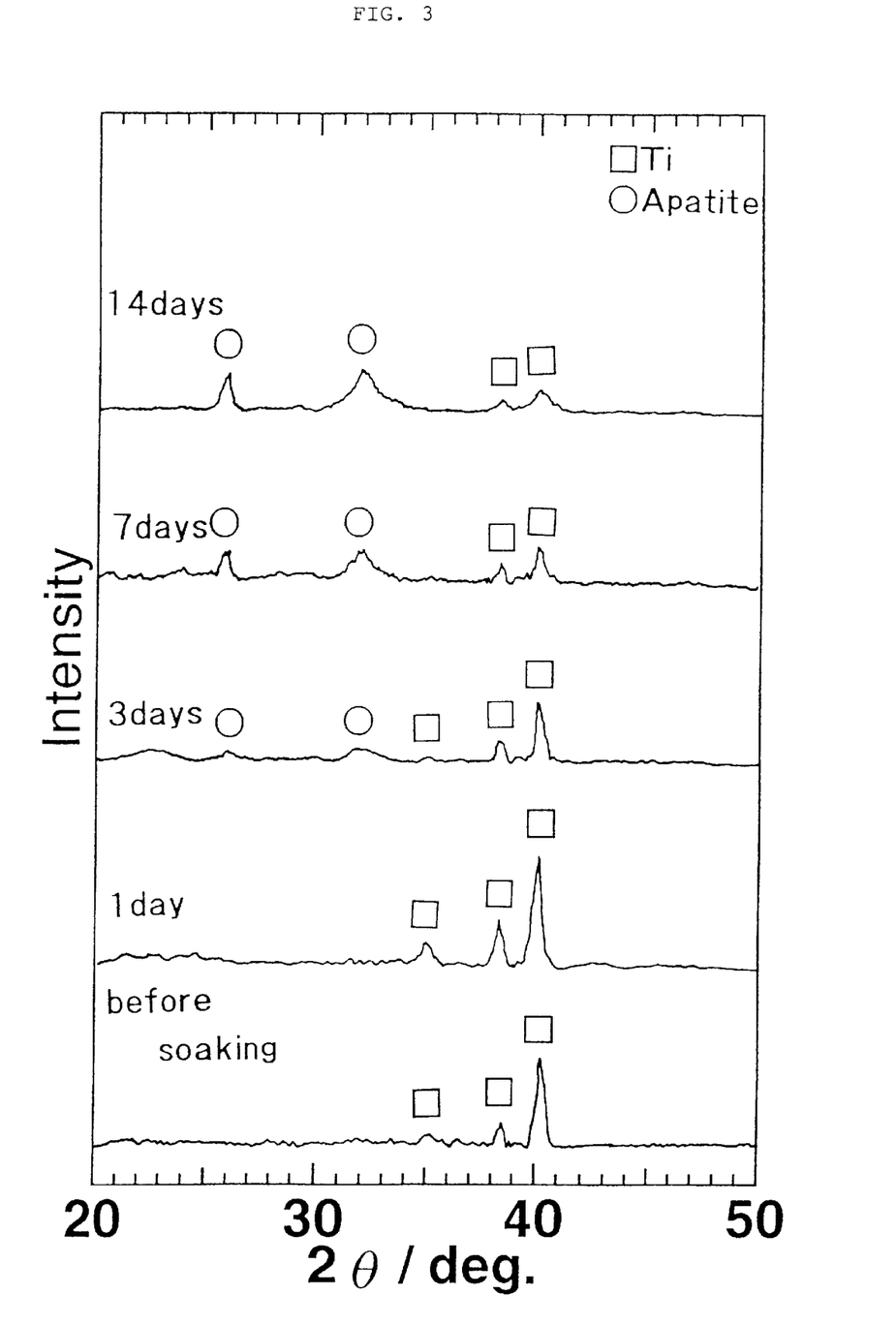
FIG. 3 shows the thin-film X ray diffraction pattern of a titanium metal plate whose surface is treated with a hydrogen peroxide aqueous solution containing Ta ions, before and after being immersed in the simulated body fluid.

The titanium metal plate that has the surface processed as described above is immersed in the 40 ml of simulated body fluid at 36.5° C. The FT-IR Reflection Spectrum {FIG. 2 (each trace is labeled with the time period of immersion in the simulated body fluid and 0 indicates the presence of apatite)} and the thin film X-ray diffraction patterns {FIG. 3 (each trace is labeled with the time period of immersion in the simulated body fluid and 0 indicates the presence of apatite)} are measured. The peaks are recognized according to the presence of apatite (1,130 cm$^{-1}$, 1,040 cm$^{-1}$, 610 cm$^{-1}$, 570 cm$^{-1}$) on the FT-IR Reflection Spectrum. Crystalline hydroxyapatite are also recognized from the peaks of 2θ=26° and 2θ=32°.

From these results, a formation of hydroxyapatite on the surface of the titanium metal plate is confirmed. The thickness of the hydroxyapatite layer is about 10 μm.

Figure 4A:
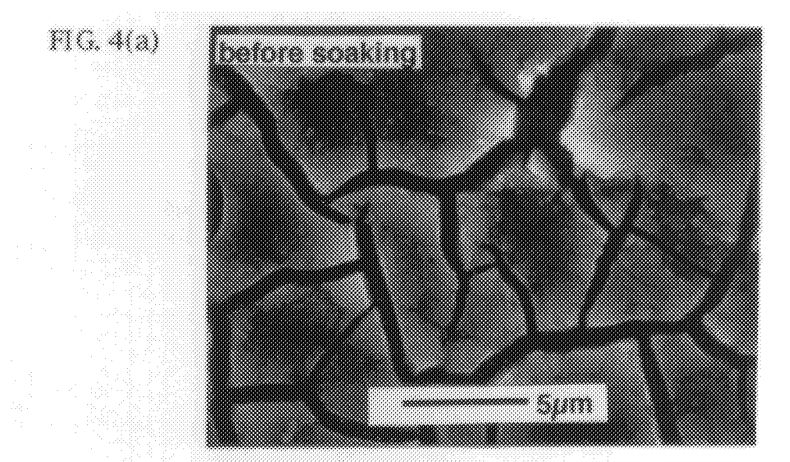
FIG. 4(a) shows the plate before being immersed in the simulated body fluid.
Figure 4B:
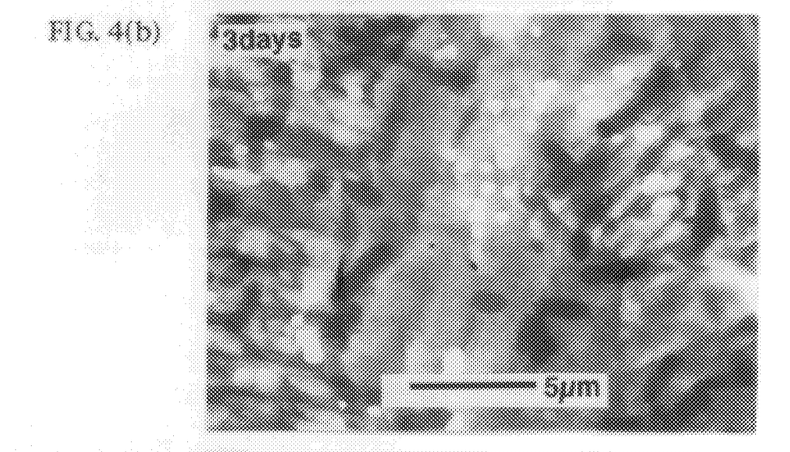
FIG. 4(b) shows the plate three days after being immersed in the simulated body fluid.
Figure 4C:
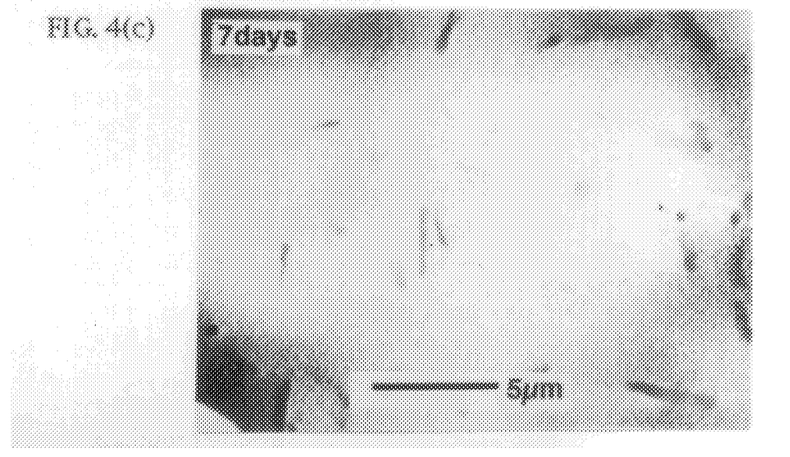
FIG. 4(c) shows the plate seven days after being immersed in the simulated body fluid.

FIG. 4 shows the scanning electron micrographs of the titanium metal plates whose surfaces were processed by a hydrogen peroxide aqueous solution containing Ta ions. FIG. 4(a) shows the plate being immersed in the simulated body fluid, and FIG. 4(b) shows the plate seven days after being immersed in the simulated body fluid. The hydroxyapatite crystals can be clearly observed covering the surface of the titanium metal plates.

Figure 5A:
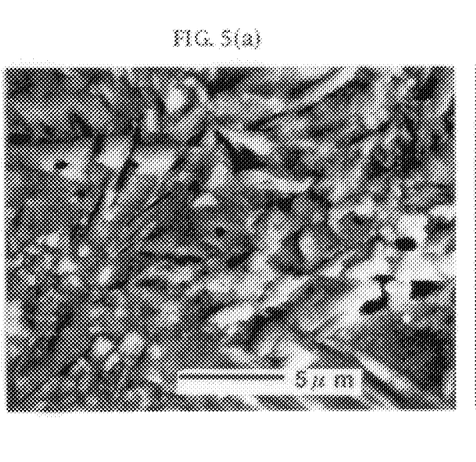
FIG. 5(a) shows the plate before being immersed in the simulated body fluid.
Figure 5B:
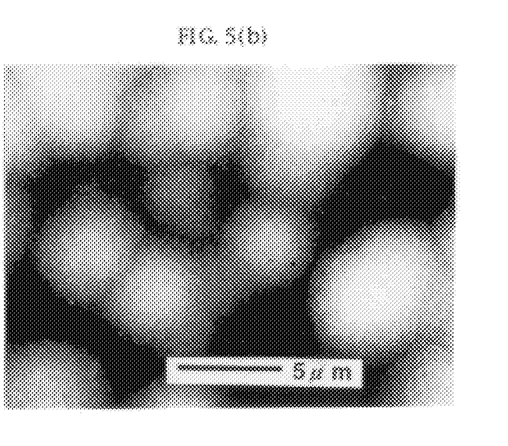
FIG. 5(b) shows the plate 14 days after being immersed in the simulated body fluid.

Embodiment using titanium metal plate processed by a hydrogen peroxide aqueous solution that contains several ions Table 2 shows the results of the measurement of the concentrations of the chemical elements and the thickness of apatite layer of the surfaces of metal plates which were processed using different types of ions added to the hydrogen peroxide aqueous solution and then immersed in the simulated body fluids for two weeks. The concentrations and thickness were measured and observed by EDX (Energy Distribution X-ray Microanalysis) and a scanning electron microscopic. FIG. 5 shows the scanning electron micrographs of the titanium metal plate in which the surface was processed using an SnCl2 containing hydrogen peroxide aqueous solution. FIG. 5(a) shows the plate before being immersed in the pseud body fluid, and FIG. 5(b) shows the plate 14 days after being immersed in the simulated body fluid. From these figures, it can be seen that: hydroxyapatite crystal covers the surface of the titanium metal plate and the crystalline hydroxyapatite forms on the surface of the titanium metal plate: it is treated with the hydrogen peroxide aqueous solution containing specific metal ions. The effect on the formation of hydroxyapatite crystal is significant when Ta or Sn ions are added to the hydrogen peroxide aqueous solution.

Embodiment using titanium metal plate processed by a hydrogen peroxide aqueous solution that contains Ta ions along with other ions The same procedure as the above was performed except that a concentration of 1 mmol/dm$^3$ of NaCl and CaCl2 along with TaCl5 ion, respectively, are added to a hydrogen peroxide aqueous solution for processing the surface of the titanium metal plate.

After soaking the titanium metal plate in which the surface is processed in 40 m$^3$ of simulated body fluid for seven days at 36.5° C., the hydroxyapatite formation is observed on the surface of the plate.

Embodiment using titanium metal plate processed by a hydrogen peroxide aqueous solution that contains Ta ions and is kept at 100° C.

The same procedure was taken to process the surface of the metal plate using a hydrogen peroxide aqueous solution containing Ta ions except that a pressure resistant container made of glass (and not stainless steel) was used and the retained temperature was 100° C.

After soaking the titanium metal plate in which the surface is processed at 100° C. in 40 m$^3$ of simulated body fluid for seven days at 36.5° C., the hydroxyapatite formation was observed on the surface of the plate.

Embodiment using a titanium alloy plate processed by a hydrogen peroxide aqueous solution that contains Ta ions The same procedure was taken as in the above procedure using a hydrogen peroxide aqueous solution that contains Ta ions therein except that a Ti-6Al-4V alloy plate is used instead of the titanium metal plate.

Figure 6A:
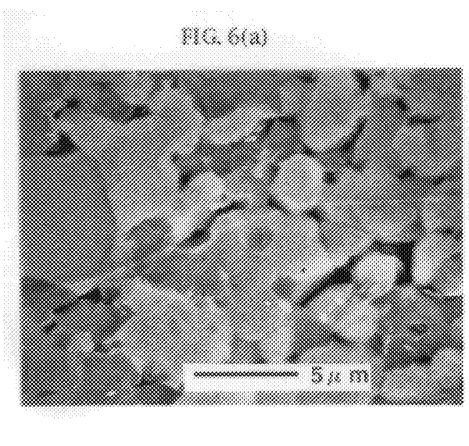
FIG. 6(a) shows the plate before being immersed in the simulated body fluid.
Figure 6B:
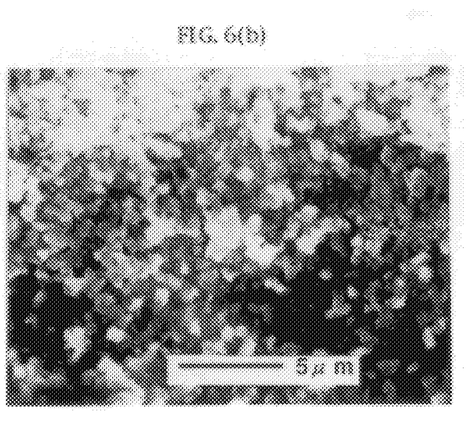
FIG. 6(b) shows the plate 14 days after being immersed in the simulated body fluid.

A Ti-6Al-4V alloy plate in which the surface is processed by the hydrogen peroxide aqueous solution containing Ta ions was immersed in 40 ml of simulated body fluid for seven days at 36.5° C. As the result of the measurement of the FT-IR Reflection Spectrum and Thin Film X-ray Diffraction, the formation of hydroxyapatite layer is confirmed on the surface of the Ti-6Al-4V alloy plate. FIG. 6 shows scanning electron micrographs of the Ti-6Al-4V alloy plate. FIG. 6(a) shows the plate before being immersed in the pseud body fluid, and FIG. 6(b) shows the plate 14 days after being immersed in the simulated body fluid. The hydroxyapatite crystals are clearly observed covering the surface of the Ti-6Al-4V alloy plate as time passes.

Figure 7A:
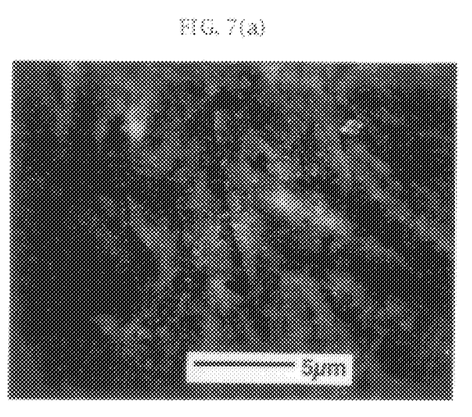
FIG. 7(a) shows the plate before being immersed in the simulated body fluid.
Figure 7B:
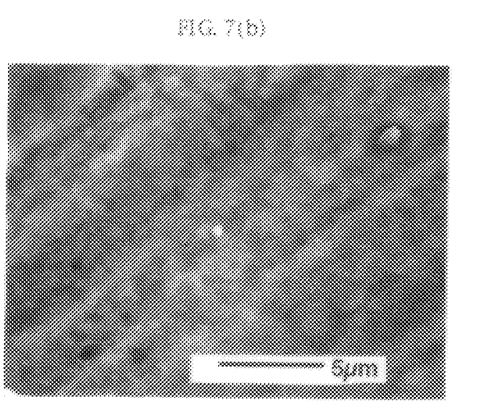
FIG. 7(b) shows the plate 14 days after being immersed in the simulated body fluid.

FIG. 7 shows a comparative example of the scanning electron micrographs of the titanium metal plate in which the surface is processed by a hydrogen peroxide aqueous solution which contains no metal ions therein. FIG. 7(a) shows the titanium metal plate before being immersed in the pseud body fluid, and FIG. 7(b) shows the plate 14 days after being immersed in the simulated body fluid. No formation of the hydroxyapatite crystal is observed.

Figure 8:
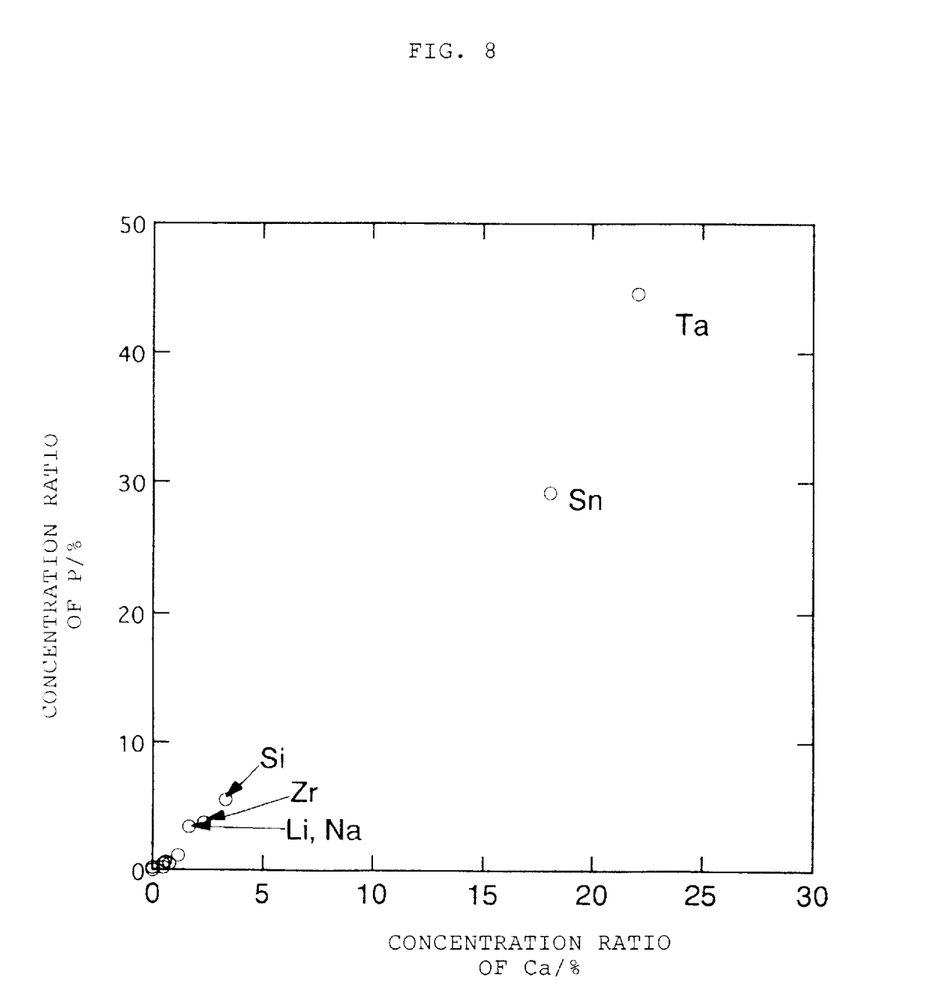
FIG. 8 shows the concentrations of Ca and P in the surface layer formed on a titanium plate which is processed by a hydrogen peroxide aqueous solution to which several ions are added, the plate having been immersed for 14 days in the simulated body fluid.

FIG. 8 shows the concentrations of chemical compounds of Ca and P in the surface layer when a titanium plate, which was processed by a hydrogen peroxide aqueous solution containing several ions, was immersed in the simulated body fluid for 14 days. The concentrations were measured by the Energy Distribution X-ray Microanalysis. From the results, it is obvious that the formation of the crystalline hydroxyapatite is promoted by the addition of ions to the hydrogen peroxide aqueous solution, especially in the cases of addition of Ta and Sn ions.

The reason why metal ions added to a hydrogen peroxide aqueous solution have a significant effect on separating apatite is not clear; however, it is considered that some hydrated oxide of the corresponding metals, which are effective for forming the apatite layer in a hydrogen peroxide aqueous solution, are formed.

Figure 9:
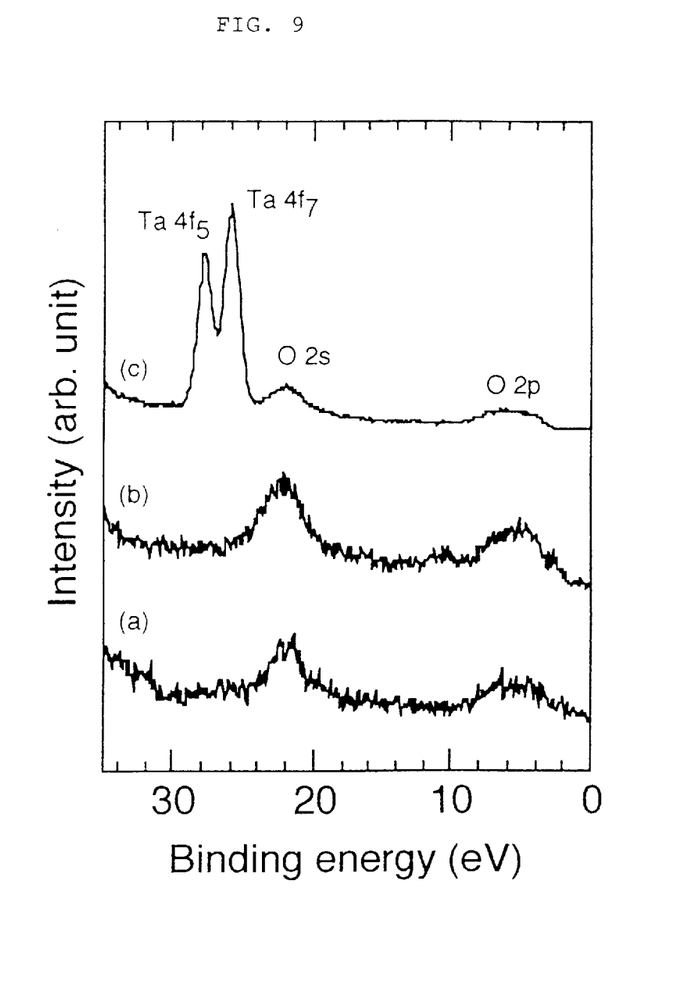
FIG. 9 shows the XPS Spectrum of the surface of a titanium metal which is processed by a hydrogen peroxide aqueous solution that contains tantalum chloride.

FIG. 9 shows the observation of the upper most surface (less than 10 nm) of titanium by XPS. The peaks for Ta4f5 is clearly observed in FIG. 9. From the results, the existence of Ta can be confirmed on the surface of the titanium. Since the titanium was processed by the Ta ion-containing hydrogen peroxide aqueous solution, a hydrated titanium oxide is considered to have been formed. The ability for forming apatite becomes absolutely higher in these cases.

Figure 10:
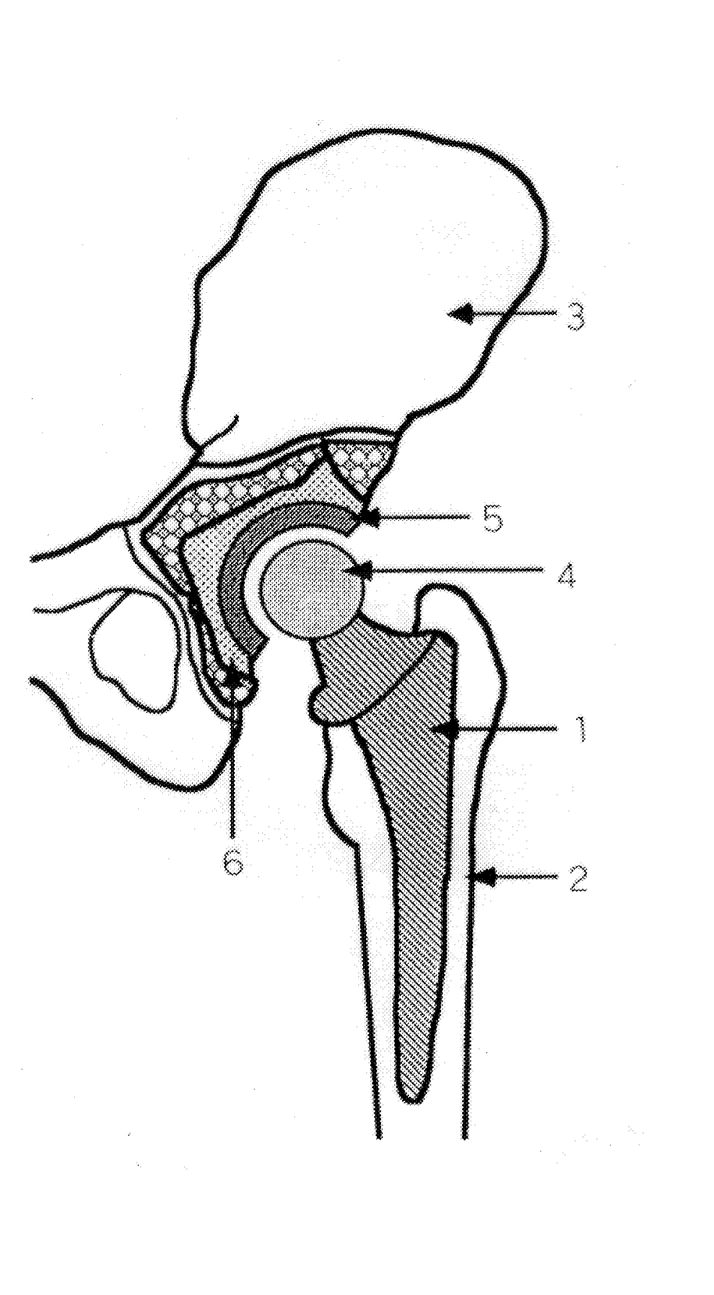
FIG. 10 shows an example showing the application of the biocompatible titanium implant of the present invention being used.

FIG. 10 shows an example of the biocompatible titanium implant 1 according to the present invention. The biocompatible titanium implant of the present invention is embedded and unified with a femur 2, which is to be connected to a pelvis 3. The biocompatible titanium implant 1 is adhered to articular head 4, whose base is made of aluminum ceramic having a disk-like cross section, and fitted into a semispherical acetabular roof 5 which is made of high concentration polyethylene. The semispherical acetabular roof 5 is adhered to pelvis 3 with MMA bone cement 6. The biocompatible titanium implant 1 of the present invention bonds firmly with femur 2 by the hydroxyapatite layer formed on its surface.

As seen from the above, according to the present invention, it is possible to provide bioactivity in a simple method to the surface of titanium material, which is superior in mechanical properties, at a low temperature such as below 100° C., and the implant can be used as the material for artificial bones which require the ability to be joined suitably with bones. Therefore, the present invention has an excellent effect on the medical industry.

TABLE 1

| IONS | CONCENTRATION (×10$^{-3}$ M) |
|---|---|
| NA$^+$ | 142.0 |
| K$^+$ | 5.0 |
| Ca$^{2+}$ | 2.5 |
| Mg$^{2+}$ | 1.5 |
| Cl$^-$ | 147.8 |
| HCO$_3^-$ | 4.2 |
| HPO$_4^{2-}$ | 1.0 |
| SO$_4^{2-}$ | 0.5 |

TABLE 2

| | ELEMENT/ATOM % | | | | | | | | | | | | | | | Ca/P ATOM RATIO | THICKNESS OF APATITE LAYER (μm) |
|---|---|---|---|---|---|---|---|---|---|---|---|---|---|---|---|---|---|
| ADDITIVES | Ti | O | Na | K | Mg | Ta | Pd | Sn | Zr | Ni | Si | V | Nb | Ca | P | | |
| NO ADDITIVES | 61.4 | 36.4 | 0.0 | 0.0 | 0.0 | 0.0 | 0.0 | 0.0 | 0.0 | 0.0 | 0.0 | 0.0 | 0.0 | 1.1 | 1.1 | 1.0 | <0.5 |
| LiNO$_3$ | 66.8 | 28.2 | 0.0 | 0.0 | 0.0 | 0.0 | 0.0 | 0.0 | 0.0 | 0.0 | 0.0 | 0.0 | 0.0 | 3.4 | 1.6 | 2.1 | 1 |
| NaCl | 67.3 | 26.3 | 1.4 | 0.0 | 0.0 | 0.0 | 0.0 | 0.0 | 0.0 | 0.0 | 0.0 | 0.0 | 0.0 | 3.4 | 1.6 | 2.1 | 1 |
| KCl | 70.2 | 29.5 | 0.0 | 0.3 | 0.0 | 0.0 | 0.0 | 0.0 | 0.0 | 0.0 | 0.0 | 0.0 | 0.0 | 0.0 | 0.0 | — | 0 |

TABLE 2-continued

| ADDITIVES | ELEMENT/ATOM % | | | | | | | | | | | | | | | Ca/P ATOM RATIO | THICKNESS OF APATITE LAYER ($\mu$m) |
| | Ti | O | Na | K | Mg | Ta | Pd | Sn | Zr | Ni | Si | V | Nb | Ca | P | | |
|---|---|---|---|---|---|---|---|---|---|---|---|---|---|---|---|---|---|
| $MgCl_2$ | 72.3 | 27.2 | 0.0 | 0.0 | 0.5 | 0.0 | 0.0 | 0.0 | 0.0 | 0.0 | 0.0 | 0.0 | 0.0 | 0.0 | 0.0 | — | 0 |
| $CaCl_2$ | 75.7 | 24.1 | 0.0 | 0.0 | 0.0 | 0.0 | 0.0 | 0.0 | 0.0 | 0.0 | 0.0 | 0.0 | 0.0 | 0.2 | 0.0 | — | 0 |
| $ZrCl_4$ | 40.4 | 53.5 | 0.0 | 0.0 | 0.0 | 0.0 | 0.0 | 0.0 | 0.1 | 0.0 | 0.0 | 0.0 | 0.0 | 3.7 | 2.3 | 1.6 | 1 |
| $VCl_3$ | 74.6 | 24.2 | 0.0 | 0.0 | 0.0 | 0.0 | 0.0 | 0.0 | 0.0 | 0.0 | 0.0 | 0.0 | 0.0 | 0.6 | 0.6 | I.0 | <0.5 |
| $NbCl_5$ | 72.8 | 25.3 | 0.0 | 0.0 | 0.0 | 0.0 | 0.0 | 0.0 | 0.0 | 0.0 | 0.0 | 0.0 | 0.6 | 0.5 | 0.7 | 0.7 | <0.5 |
| $TaCl_5$ | 0.5 | 31.7 | 0.0 | 0.0 | 0.0 | 1.1 | 0.0 | 0.0 | 0.0 | 0.0 | 0.0 | 0.0 | 0.0 | 44.6 | 22.1 | 2.0 | 10 |
| $NiCl_2$ | 75.2 | 22.4 | 0.0 | 0.0 | 0.0 | 0.0 | 0.0 | 0.0 | 0.0 | 1.1 | 0.0 | 0.0 | 0.0 | 0.2 | 0.5 | 0.5 | <0.5 |
| $PdCl_2$ | 57.0 | 41.5 | 0.0 | 0.0 | 0.0 | 0.0 | 0.6 | 0.0 | 0.0 | 0.0 | 0.0 | 0.0 | 0.0 | 0.5 | 0.5 | 1.0 | <0.5 |
| $SiCl_4$ | 38.1 | 52.8 | 0.0 | 0.0 | 0.0 | 00 | 00 | 0.0 | 0.0 | 0.0 | 0.4 | 0.0 | 0.0 | 5.4 | 3.3 | 1.7 | 1 |
| $SnCl_2$ | 3.0 | 49.0 | 0.0 | 0.0 | 0.0 | 0.0 | 0.0 | 0.4 | 0.0 | 0.0 | 0.0 | 0.0 | 0.0 | 29.1 | 18.1 | 1.6 | 10 |
| NOT PROCESSED | 81.6 | 18.4 | 0.0 | 0.0 | 0.0 | 0.0 | 0.0 | 0.0 | 0.0 | 0.0 | 0.0 | 0.0 | 0.0 | 0.0 | 0.0 | — | 0 |

$VCl_3$ & $NbCl_5$ PROCESSED IN HYDROGEN PEROXIDE AQUEOUS SOLUTION FOR 30 MINUTES

We claim:

1. A biocompatible titanium implant with increased bioactivity comprising a covering layer on a surface thereof of hydrated titania gel that contains metal ions, said covering layer having increased affinity for apatite formation, said titanium implant being processed by a hydrogen peroxide aqueous solution which contains metal ions, said solution promotes a reaction on the surface of said titanium implant forming said covering layer whereby a layer of apatite is formed on said biocompatible titanium implant when placed in contact with body fluid and tissues to unify the titanium implant with the body tissues through said apatite layer, and wherein said metal ions are at least one selected from the group consisting of Ta and Sn.

2. A biocompatible titanium implant with increased bioactivity comprising a layer on an exterior surface thereof, said layer being a hydrated titania gel obtained by immersing the titanium implant in a hydrogen peroxide aqueous solution, said solution contains metal ions selected from the group consisting of Ta and Sn whereby a layer of apatite is formed on said biocompatible titanium implant when placed in contact with body fluids and tissues to unify the titanium implant with the body tissues through said apatite layer.

3. A biocompatible titanium implant according to claim 1, wherein said metal ions are at least one selected from the group consisting of Ta, Sn, Ti, Si, Zr, Li and Na.

4. A biocompatible titanium implant according to claim 2, wherein a concentration of said hydrogen peroxide aqueous solution is 5–30% by weight.

5. A biocompatible titanium implant according to claim 3, wherein a temperature of said hydrogen peroxide aqueous solution is 30°–90° C.

* * * * *